United States Patent [19]

Landis et al.

[11] Patent Number: 4,648,393

[45] Date of Patent: Mar. 10, 1987

[54] BREATH ACTIVATED MEDICATION SPRAY

[75] Inventors: Robert Landis, New York, N.Y.; Joseph E. Kassay, Laurence Harbor, N.J.

[73] Assignee: Ackrad Laboratories, Inc., Cranford, N.J.

[21] Appl. No.: 667,544

[22] Filed: Nov. 2, 1984

[51] Int. Cl.$^4$ .............................................. A61M 15/00
[52] U.S. Cl. .................................................. 128/200.23
[58] Field of Search .................... 128/200.14, 200.23, 128/204.23, 204.21, 203.15

[56] References Cited

U.S. PATENT DOCUMENTS

| | | | |
|---|---|---|---|
| 3,566,387 | 2/1971 | Schoener et al. | 128/204.23 |
| 3,584,621 | 6/1971 | Bird | 128/200.18 |
| 3,636,949 | 1/1972 | Kropp | 128/200.23 |
| 3,812,854 | 5/1974 | Michaels et al. | 128/200.16 |
| 4,106,503 | 8/1978 | Rosenthal et al. | 128/200.18 |
| 4,334,531 | 6/1982 | Reichl et al. | 128/200.14 |

Primary Examiner—Henry J. Recla
Attorney, Agent, or Firm—Lackenbach Siegel Marzullo & Aronson

[57] ABSTRACT

An inhalation device for dispensing a medicament from a metered dosage cartridge that includes a hand-held housing having a mouthpiece and a passageway for ambient air, a triggering mechanism mounted in the housing, a biasing device for moving the cartridge to operative relationship with the passageway upon activation by the triggering mechanism, and a battery-powered circuit in the housing including a switch associated with the passageway and a solenoid operated mechanism secured to the housing for activating the trigger mechanism, with the switch acting to close the circuit and so activate the solenoid so as to activate the trigger mechanism and the biasing device so that the cartridge positions an activated outlet pin into the passageway. The switch is activated by the pressure of the passage of air drawn through the passageway by the inhaling action of the patient.

15 Claims, 4 Drawing Figures

BREATH ACTIVATED MEDICATION SPRAY

BACKGROUND OF THE INVENTION

The present invention relates to an inhalation device, whereby the action of inhaling activates a vial containing medication which then releases a metered dose or predetermined amount of medication directly into the patient's mouth.

Heretofore, devices for inhaling medicines, such as liquid medicaments into the lungs under pressure action were not activated by an inhaling action of the user. Such prior art devices are exemplified by the following U.S. Pat. Nos.:

Mobley, 1,614,532
Pitesky et al. 3,776,227
Hogg, 3,326,231
Updegraff, 3,045,671
Johnston, 3,012,694
Doak, 2,970,594
Hamilton et al. 2,852,023
Levitt, 2,428,425
Kitrell, 4,297,999
Kropfhammer, 3,964,478
Jones, 1,176,146
Schroder, 1,693,730
Sholes, 2,119,446
Olowinski, 2,510,712

U.S. Pat. No. 1,614,532 issued to Mobley on Jan. 18, 1927 discloses a device for applying liquid medicaments under pressure whereby a canister containing medicament whereby a canister containing medicaments under pressure is opened by a small pin which is manually operated by the thumb or a finger of the user. The released liquid travels through a spirally whirling motion and is ejected as a stream which is inhaled by the user.

U.S. Pat. No. 3,776,227 issued to Pitesky et al., on Dec. 4, 1973 discloses a device whereby a cartridge containing gas under pressure is opened by a pin which results in a flow of released gas. The opening is activated by manually rotating a housing containing a pressurized container and valve-supporting head relative to one another until the cartridge is punctured.

U.S. Pat. No. 3,326,231 issued to Hogg on June 20, 1967 discloses a fluid regulating valve mechanism whereby the flow rate of a fluid released from a puncturable storage container which is ultimately inhaled by the user is metered by regulating the size of the needle valve formed when a pin pierces the container. This process is started by manually depressing an actuator so that the pin will pierce into the compressed container.

U.S. Pat. No. 3,045,671 issued to Updegraff on July 24, 1962 discloses a device whereby a cartridge containing gas under pressure is pierced by a hollow pin or needle which releases a gas which is ultimately inhaled by the user. The piercing of the pressurized capsule containing the gas is performed by manually screwing the pin into the cartridge's seal.

U.S. Pat. No. 3,012,694 issued to Johnston on Dec. 12, 1961 discloses a gas dispensing device whereby gas contained in a pressurized container is released when a point punctures the container. A handwheel manually operates a threaded member which moves the capsule closer to the point which eventually punctures the container. A sleeve may manually be moved to restrict the opening of the hole and thus regulate the flow of gas to be inhaled.

U.S. Pat. No. 2,970,594 issued to Doak on Feb. 7, 1961 discloses a device whereby gas contained in a pressurized container is released for ultimate inhaling by the user when a pin pierces the container. The piercing action is regulated by the closing of the door on the chamber which holds the capsule which, in turn, manually forces the pin onto the capsule, when the capsule is so pierced the gas.

U.S. Pat. No. 2,852,023 issued to Hamilton et al. on Sept. 16, 1958 discloses a closed system whereby gas contained in a pressurized capsule is released by pulling a ring which, in turn, causes a perforater to move upward and penetrate into the capsule. The escaped gas can then be inhaled. The chamber into which the gas escapes contains a chemical which will remove carbon dioxide from the exhaled breath of the user. The exhaled breath can thus be inhaled.

U.S. Pat. No. 2,428,425 issued to Levitt on Oct. 7, 1947 discloses a portable oxygen breather whereby gas contained under pressure in a capsule is released when a pin pierces the capsule by means of a manually operated screwing device.

U.S. Pat. No. 4,297,999 issued to Kitrell on Nov. 3, 1981 discloses an inhaler whereby a bellows-type pump is utilized to pump oxygen or atmospheric gas into the inhaler's lungs.

U.S. Pat. No. 3,964,478 issued to Kropfhammer on June 22, 1976 discloses a device whereby a value is manually opened, which permits oxygen to flow into an applicator to be eventually inhaled.

U.S. Pat. No. 1,176,446 issued to Jones on Mar. 21, 1916 discloses a device whereby the amount of anesthetic inhaled can be regulated by the inhaler by a pressing movement of the user's thumb. By so working with the thumb, the user can either open or close an air intake valve from which the gas tos be inhaled is supplied.

U.S. Pat. No. 1,693,730 issued to Schroder on Dec. 4, 1928 discloses a device whereby the quantity of air inhaled corresponds to the depth of the user's breathing. There are no pins or piercing devices needed to dispense a predetermined amount of gas. The flow of the compressed gas creates a vacuum or partial vacuum which draws medicament into the device by droplets. These are then driven into the nozzle and eventually inhaled in a fine spray.

U.S. Pat. No. 2,119,446 issued to Sholes on May 31, 1938 discloses an apparatus for self-administration of anesthestic whereby the inhaler manually alternately compresses and/or releases a contractible and/or expansable rubber ball which controls the supply of gas to the inhaler.

U.S. Pat. No. 2,510,712 issued to Olowinski on June 6, 1950 discloses a portable gas dispenser which dispenses a gas under the manual control of the user, including a means for adding medicaments to the gas dispensed. The valve mechanism which controls the flow of the compressed gas contained in a flask is controlled by manual movement of a rotatable valve plug. A manual threading action opens the valve which allows the gas to escape by controlled means. A receptable can be filled with medicament which is inhaled with the gas.

None of the above-mentioned references, show the use of an inhalation device which is solely activated by the action of inhalation.

SUMMARY OF THE INVENTION

It is therefore an object of this invention to provide for a device in which the action of inhaling activates a series of reactions or steps whereby a vial containing medication is opened by a pin, thus releasing a metered dose or predetermined amount of medication which is directly inhaled into the user's mouth.

Another object of the invention is to provide for a manual override which causes the device to be activated apart from the inhaling action of the user.

Yet another object of the invention is to provide for a device which is simple in construction and one which is relatively inexpensive to produce.

Another object of the invention is to provide for a device which is portable and small enough in scale to be carried easily by the user, such as for example in one's pocket.

A BRIEF DESCRIPTION OF THE DRAWINGS

FIG. 1 is a perspective view of the device in a "standby" or locked position; with the air intake is illustrated by arrows, FIG. 2 is a planar view of the device in the "standby" or cocked position, and showing in a break-away illustration the curved lever arm, FIG. 3 is a planar view of the device similar to that of FIG. 2, but showing the device in the activated position; and FIG. 4 is a cross-sectional view of the mouthpiece means.

DESCRIPTION OF THE PREFERRED EMBODIMENTS

Figure 1:
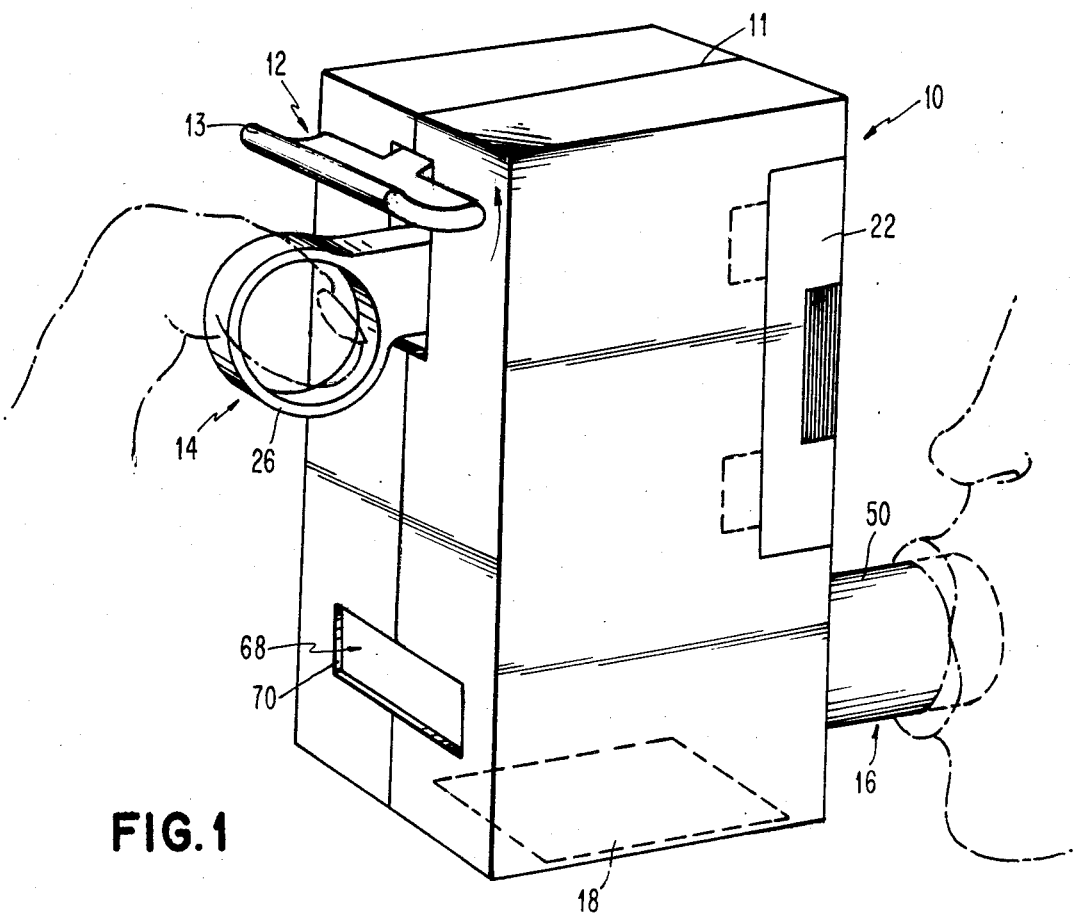
Figure 2:
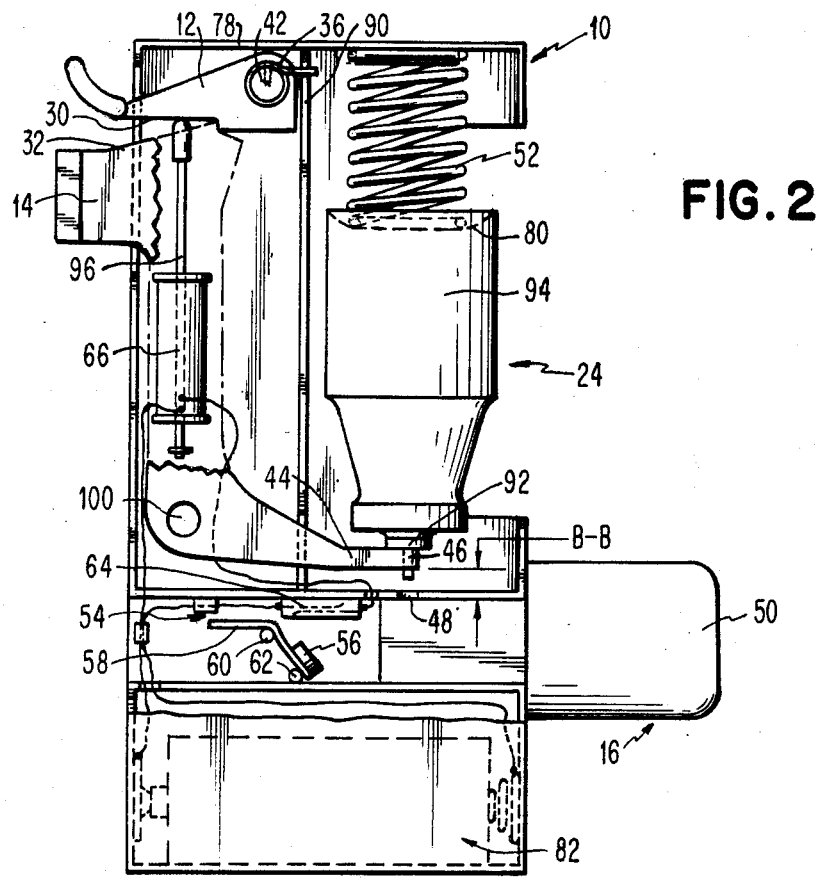
Figure 3:
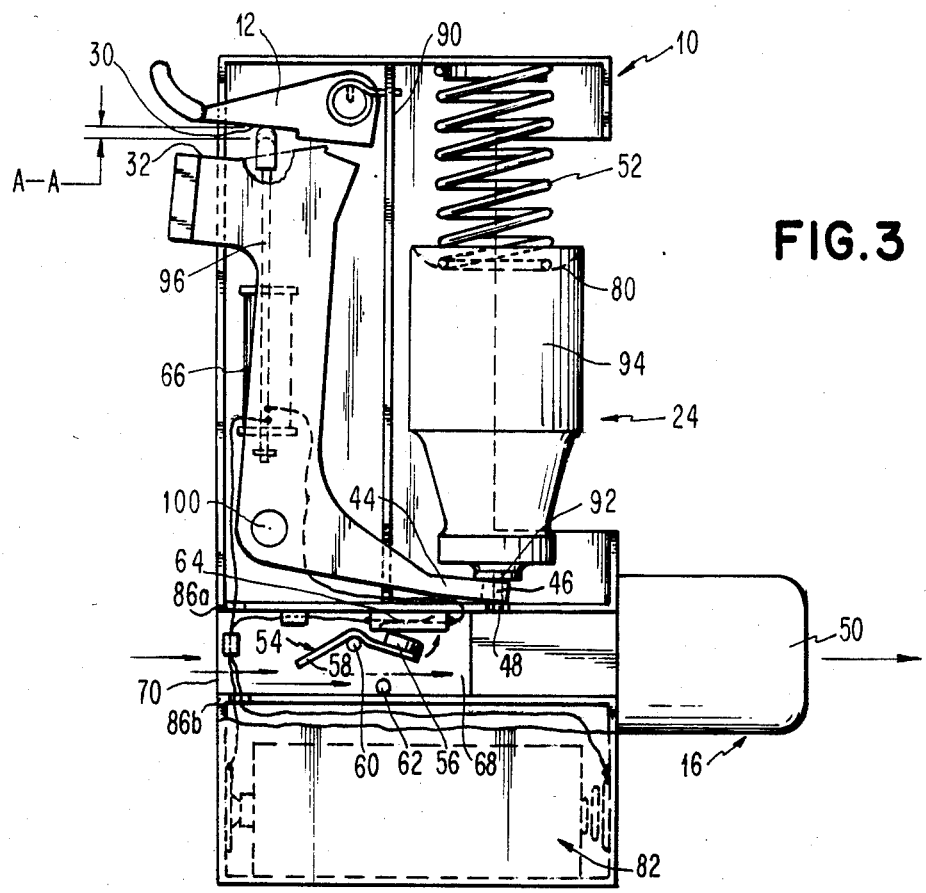

FIG. 1 shows a perspective view of the device constructed in accordance with the principles of the present invention which embodies a housing or case means 10, preferably composed of plastic, which is openable suitably along a longitudinal axial seam 11, whereby said case means 10 is divided into halves, one of which is best shown in FIGS. 2 and 3. A straight lever arm means 12 comprising a T-shaped handle portion 13, is cooperatively associated with an L-shaped curved lever arm means 14 by means of notched surfaces. The lever arm means 14 comprises a handle portion 26, suitably provided with a finger loop, so that said straight lever arm means 12 and said curved lever arm means 14 are disposed exteriorly of the case means 10, so that they are easily accessible to the user when the device is in use. The user manually cocks the device by outwardly pulling the curved lever arm means 14 which in turn raises slightly the straight lever arms means 12. The device is now a "standby" or cocked position. It is apparent from FIG. 3, when the device is in the uncocked position, same is akin to a safety feature since the device cannot be accidentally set off while not in use. A suitably removable mouthpiece means 16 mounted on the case means 10 is easily accessible to the user, so that the orifice portion 50 of said mouth piece means 16 can be placed into one's mouth while holding the device in a hand while at the same time cocking the apparatus prior to use. The mouthpiece means 16 is removable for cleaning and it may be provided with a friction fit. Access means for the medicine cartridge may be provided in the case means 10, such as by panel 22 which may be suitably removed from said case means 10 in order to make the cartridge compartment 24 easily accessible for replacing a cartridge 24, as best shown in FIGS. 2 and 3. Another panel 18 of said case means 10 provides easy access to a suitable power source, such as a battery (shown in phantom).

By inhaling through said mouthpiece means 16, atmospheric air is taken in through intake opening 70 of conduit 68 in case means 10. By so inhaling, the user activates a series of steps which culminate when a predetermined metered amount of medicament stored in a cartridge is mixed with air and is ultimately inhaled by the user.

With a dead battery, the device can also be manually operated by the user by pushing T-shaped handle portion 13 of said straight lever arm means 12 in an upwardly direction, as shown by an arrow, thus disengaging said notched interfaced straight lever arm means 12 from the curved lever arm means 14, which, in turn, activates a series of steps, whereby a predetermined metered amount of medicament is ultimately inhaled by the user.

FIG. 2 illustrates a planar view of the inner components of the device of FIG. 1, and the device is illustrated in the cocked position.

The notched edge portion of said straight lever arm means 12 engages the notched edge portion 32 of said curved lever arm means 14, which allows for the notched interfaced locking of said straight and curved lever arms, 12 and 14, respectively.

Suitable spring means 36, such as a torsion spring, fixably attached at one end to a central wall portion 74 of said case means 10, and its turns are disposed around a conforming cylindrical outwardly projecting pivotal shaft mount portion 42 of said straight lever arm means 12, so as to exert a torsion which forces said straight level arm means 12 against said curved lever arm means 14. Thus, the interfaced notched portion 30 of said straight lever arm means 12 engages against said notched edge portion 32 of said curved lever arm means 14. The other end of the spring means 36 extends into a blind hole and is thereby connected to the shaft portion 42 for urging same in a counterclockwise direction, as shown by the reference arrowhead in FIG. 2.

Alternatively, the non-movable end of the spring means 36 can be fixably attached to other proximate wall surface portions of said case means 10, such as, upper wall surface 78.

Pin and/or tube portion 46 of said cartridge means 24 is retractably disposed with respect to disc portion 92 of the cartridge means 24 and is seated within a recessed end portion 44 of said curved lever arm means 14, preferably U-shaped in form to fascilitate replacement of the cartridge. The cartridge is conventionally available and is of a standard size, and the pharmaceutical industry manufactures such cartridges with a variety of medicaments. Disc portion 92 of said cartridge means 24 sits atop the U-shaped recessed end portion 44 of said curved lever arm means 14.

Figure 4:
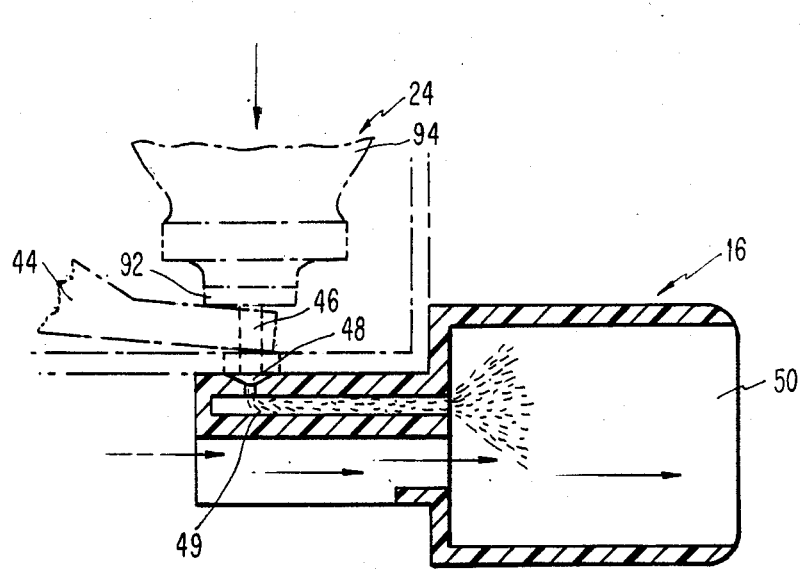

While an end of said curved lever arm means 14 is preferably U-shaped, an alternate construction is possible, such as, a circular opening in which the diameter of said circular opening approximates the diameter of the cylindrical pin portion 46. The pin portion 46 of said cartridge means 24 is directly aligned with an aperture in the conduit portion 48 of said mouthpiece means 16, as best shown in FIG. 4.

Compression spring means 52 securely exerts a downward force upon the depressed disc-like edge portion 80 of canister portion 94 of the cartridge means 24, which tensionally holds said cartridge means 24 against said U-shaped recessed end portion 44 of said curved lever arm means 14.

Angled door means 54, having an attached magnet 56, and a stop portion 58 is rotatably mounted about pivot means 60. The stop portion 58 of the door means leans up against the passageway wall when the air conduit is closed. The magnet 56 of the door means 54 is attracted to the metallic means 62, suitably in the form of a pin, so as to restrain the door means 54 from moving. If the door means 54 moves, the magnet 56 activates switch means 64, of electric circuitry which, in turn, energizes solenoid means 66. Alternate means to frictionally retain said door means 54 in a fixed position could also be utilized, but said magnet 56 is necessary in the embodiment shown herein as the contacts of a reed switch as shown are closed by the magnet 56 when it is juxtaposed or in proximity to said reed switch means 64. Thus, switch means 64 of FIG. 2 is shown in open position. Solenoid means 66 is shown in position behind the curved lever arm means 14.

FIG. 3 illustrates the components of the device in an activated position. Inhaling through the orifice 50 of mouthpiece means 16 creates an inwardly flow of air (as shown by the referenced arrow) through conduit 68 of case means 10 which is defined by wall portions 86 (a & b), so that atmospheric air enters said conduit 68 of said case means 10 inwardly through end aperture 70, and the air flows against door means 54 and exits outwardly through said mouthpiece means 16. The force of said air flow against said door means 54, causes the magnet 56 of the door means 54 to disengage from the metallic arresting means 62 and to rotate and pass the air through the passageway, so as to cause said magnet 56 of said door means 54 to come into proximity with the switch means 64 causing the adjacently disposed contacts of said switch means 64 to close the electric series circuit and thereby activate the solenoid 66. Switch means 64 is preferably of the reed type, however, other alternate types of switch means may be employed in the practice of the invention, along with suitable door means for closing or activating such alternate switch device.

The closing of said switch means 64, completes a series type circuit comprising a battery housed in battery compartment 82 of said case means 10, a switch and a solenoid, and such circuit allows for the flow of electrical current to activate the solenoid means 66.

When in the activated position, the plunger portion 96 of said solenoid means 66, moves outwardly from said solenoid means 66 which causes said plunger portion 96 to strike the straight lever arm means 12. This in turn, causes the notched edged portion 30 of said straight lever arm means 12 to disengage from said notched edged portion 32 of said curved lever arm means 14, and thereafter the straight lever arm means 12 rotates in a clockwise direction, as shown by the reference arrow in FIG. 3. The plunger 96 travels a suitable distance A—A which is of sufficient length to completely disengage the interacting lever arms.

In the disengagement position, the spring means 52 exerts a downward force upon the cartridge means 24, which causes said curved lever arm means 14 which is mounted upon a suitable shaft 100 to rotate in a clockwise direction, so that said pin portion 46 of said cartridge means 24 moves a suitable distance B—B as shown in FIG. 2, and thus strikes a recessed or countersunk bore formed in an end of the conduit portion 48 of the mouthpiece 16 which is integrally formed with the mouthpiece 16. As best shown in FIGS. 3 and 4, when said pin portion 46 of said cartridge means 24 strikes the bore of said mouthpiece means 16, the pin portion 46 of said cartridge means 16 moves into the cartridge means 24, thereby permitting a predetermined or metered amount of a medicament to be released into said conduit 48 and passageway 49 of said mouthpiece means 16 and subsequently into the mouthpiece 16, where said medicament is mixed with the air flowing through conduit 68 of said case means 10, and then the mixture is inhaled by the user.

After inhalation ceases, the flow of air through conduit portion 68 of said case means 10 stops, and the metallic retaining means 62 engages the pivoted door means 54 due to gravatational forces returning the door to its closed position, and thus the magnet 56 agains holds the door 54 in a stationary inoperative position. In such position, the magnet 56 can not come into close proximity with said switch means 64, which would otherwise close the circuit and cause a steady and/or intermittant drain of the battery.

Although the present invention has been described in some detail by way of illustration and example, for purposes of clarity and understanding, it will, of course, be understood that various changes and modifications may be made in the form, details and arrangements of parts without departing from the scope of the invention as set forth in the following claims:

We claim:

1. An inhalation device for dispensing a medicament to a patient from a metered dosage cartridge, comprising:

a housing adapted to be held by hand;

said housing having a mouthpiece and a connecting passageway communicating with said mouthpiece for ambient air to be inhaled by said patient;

triggering means supported by said housing, said housing including recess means for receiving said metered dosage cartridge between said triggering means and said housing, said triggering means being movable to a first position for moving said cartridge to a non-operative position and to a second position for permitting said cartridge to move to an operative position;

biasing means in said housing for biasing said cartridge against said triggering means and for moving the cartridge to said operating position upon activation of said triggering means; and battery powered circuit means positioned in said housing including switch means positioned in association with said passageway and solenoid means secured to said housing for activating said triggering means;

the cartridge including pin means communicating with said passageway for releasing said medicament from the cartridge to said passageway upon activation of said triggering means;

said switch means being for closing said circuit and thus activating said solenoid means and thereupon activating said triggering means from said first to said second position thereby causing said biasing means to move said cartridge to said operating position thus dispensing a metered amount of said dosage into said passageway from the cartridge, said switch means being activated by a decrease in pressure in said passageway generated by the inhaling action of said patient.

2. A device as claimed in claim 1, wherein said switch means is a reed switch.

3. A device as claimed in claim 2, wherein said reed switch is activated by a movable magnet.

4. A device as claimed in claim 1, wherein said triggering means comprises a pair of lever arm means.

5. A device as claimed in claim 4, wherein said pair of lever arm means are notched so as to be latchable.

6. A device as claimed in claim 4, wherein one of said pair of lever arm means seats and holds in position said cartridge means in a yoke-like fork.

7. A device as claimed in claim 6, wherein said aperture is a circular hole approximately equal to the diameter of said pin means.

8. A device as claimed in claim 6, wherein the opposite end of said one of said pair of lever arm means is provided with a finger loop.

9. A device as claimed in claim 6, wherein the opposite end of said one of said pair of lever arm means is T-shaped at the tip portion so as to be manipulated by one's finger.

10. A device as claimed in claim 6, wherein said lever arm means are interfaced by notching means which are adapted to be manually overridden.

11. A device as claimed in claim 10, wherein the overriding action is performed by forcing said lever arm means apart.

12. A device as claimed in claim 6, wherein said pair of lever arm means comprises a straight lever arm and a curved lever arm, with the curved lever arm being said yoke-like fork; and said straight lever arm means is biased by means of a torsional spring in a direction so as to constantly interface said pair of lever arm means.

13. A device as claimed in claim 1, wherein said biased means for supporting said cartridge means is a compression spring.

14. A device as claimed in claim 1, wherein said switch means including pivotable door means having a permanent magnet for magnetically attracting contacts of said switch means for closing same so as to energize said circuit means when a user inhales through said mouthpiece.

15. A device as claimed in claim 14, wherein said door means and said mouthpiece are located within said connecting passageway of case means forming said hand held unit.

* * * * *